US012605418B2

(12) United States Patent
Tadigoppula et al.

(10) Patent No.: US 12,605,418 B2
(45) Date of Patent: Apr. 21, 2026

(54) **CHEBULINIC ACID AND ITS ENRICHED FRACTION FROM THE FRUITS OF *TERMINALIA CHEBULA* FOR TREATMENT OF BENIGN PROSTATIC HYPERPLASIA (BPH) AND ITS PREPARATION THEREOF**

(71) Applicant: COUNCIL OF SCIENTIFIC AND INDUSTRIAL RESEARCH, New Delhi (IN)

(72) Inventors: Narender Tadigoppula, Lucknow (IN); Monika Sachdev, Lucknow (IN); Rabi Shankar Bhatta, Lucknow (IN); Srikanta Kumar Rath, Lucknow (IN); Prabhat Ranjan Mishra, Lucknow (IN); Preeti Rastogi, Lucknow (IN); Tripti Mishra, Lucknow (IN); Ankit Kumar Agrawal, Lucknow (IN); Deependra Singh, Lucknow (IN); Saurabh Kumar, Lucknow (IN); Bilal Ahmad Hakim, Lucknow (IN); Sarvesh Kumar Verma, Lucknow (IN); Arpon Biswas, Lucknow (IN); Sandeep Urandur, Lucknow (IN); Sonam Kanchan, Lucknow (IN)

(73) Assignee: COUNCIL OF SCIENTIFIC AND INDUSTRIAL RESEARCH (IN)

( * ) Notice: Subject to any disclaimer, the term of this patent is extended or adjusted under 35 U.S.C. 154(b) by 420 days.

(21) Appl. No.: 18/025,803

(22) PCT Filed: Sep. 13, 2021

(86) PCT No.: PCT/IN2021/050898
§ 371 (c)(1),
(2) Date: Mar. 10, 2023

(87) PCT Pub. No.: WO2022/054100
PCT Pub. Date: Mar. 17, 2022

(65) Prior Publication Data

US 2023/0355695 A1 Nov. 9, 2023

(30) Foreign Application Priority Data

Sep. 12, 2020 (IN) ............................. 202011039625

(51) Int. Cl.
*A61K 36/185* (2006.01)
*A61K 9/107* (2006.01)
(Continued)

(52) U.S. Cl.
CPC .......... *A61K 36/185* (2013.01); *A61K 9/1075* (2013.01); *A61K 31/366* (2013.01);
(Continued)

(58) Field of Classification Search
None
See application file for complete search history.

(56) References Cited

U.S. PATENT DOCUMENTS

| | | | | |
|---|---|---|---|---|
| 9,750,778 | B2 | 9/2017 | Kalidindi et al. | |
| 2006/0257507 | A1 | 11/2006 | Doshi et al. | |
| 2013/0266676 | A1 * | 10/2013 | Ghosal ................ | A61K 36/185 424/769 |

FOREIGN PATENT DOCUMENTS

| | | | |
|---|---|---|---|
| WO | 2013155175 | A1 | 10/2013 |
| WO | 2019186355 | A1 | 10/2019 |

OTHER PUBLICATIONS

Enlarged Prostate (Benign Prostatic Hyperplasia, NIH, National Institute of Diabetes and Digestive and Kidney Disease, accessed May 20, 2025).*

(Continued)

*Primary Examiner* — Melissa S Mercier
(74) *Attorney, Agent, or Firm* — BELLES KATZ LLC

(57) ABSTRACT

The present invention relates to the beneficial effect of Chebulinic acid (CA) and its enriched standardized fraction (Continued)

(CAEF) isolated/prepared from the fruits of *Terminalia chebula* for the management of Benign Prostatic Hyperplasia respectively. Further, it relates to a novel, convenient and economically viable method for the isolation of chebulinic acid (CA) and ellagic acid (EA) from the dried and powdered fruits of *T. chebula* without using any expensive and tedious chromatographic techniques such as HPLC, column chromatography, resins etc.

12 Claims, 10 Drawing Sheets

(51) Int. Cl.

*A61K 31/366* (2006.01)
*A61K 47/10* (2017.01)
*A61K 47/12* (2006.01)
*A61K 47/26* (2006.01)
*A61K 47/44* (2017.01)
*A61P 13/08* (2006.01)

(52) U.S. Cl.

CPC .............. *A61K 47/10* (2013.01); *A61K 47/12* (2013.01); *A61K 47/26* (2013.01); *A61K 47/44* (2013.01); *A61P 13/08* (2018.01); *A61K 2236/15* (2013.01); *A61K 2236/333* (2013.01); *A61K 2236/51* (2013.01); *A61K 2236/53* (2013.01)

(56) References Cited

OTHER PUBLICATIONS

International Search Report issued in PCT/IN2021/050898 on Mar. 21, 2021.
Written Opinion of the International Searching Authority issued in PCT/IN2021/050898 on Mar. 21, 2021.
Abdelaziz S.A. Abuelsaad, et al., Life Sciences 93 (2013) 714-722, Antimicrobial and immunomodulating activities of hesperidin and ellagic acid against diarrheic Aeromonas hydrophila in a murine model, journal homepage: www.elsevier.com/locate/lifescience.
Anam, et al., α-Glucosidase Inhibitor Activity in *Terminalia* Species, International Journal of Pharmacology 5(4): 277-280, 2009.
Arya, et al., Antioxidant and Hypoglycemic Actvities of Leaf Extracts of Three Popular *Terminalia* Species, E-Journal of Chemistry (2012) 9: 883-892; K. Anam et al. International Journal of Pharmacology (2009) 5: 277-280; T. Veni et al., J Parasit Dis (2017) 41: 693-702).
Badmaev, et al., Protection of Epithelial Cells against Influenza A Virus by a Plant Derived Biological Response Modifier Ledretan-96, Phytotherapy Research, Phytother. Res. 14, 245-249 (2000).
Beiraghdar, et al. (2017) A two-week, double-blind, placebo-controlled trial of Viola odorata, Echium amoenum and Physalis alkekengi mixture in symptomatic benign prostate hyperplasia (BPH) men, Pharmaceutical Biology, 55:1, 1800-1805, DOI: 10.1080/13880209.2017.1328445.
CG Roehrborn, Pathology of benign prostatic hyperplasia, International Journal of Impotence Research (2008).
Chhabra, et al., Chebulinic Acid Isolated From the Fruits of *Terminalia chebula* Specifically Induces Apoptosis in Acute Myeloid Leukemia Cells, Phytotherapy Research, Phytother. Res. (2017), Published online in Wiley Online Library, (wileyonlinelibrary.com).
Dhanani, et al., A Validated High-Performance Liquid Chromatography Method for Determination of Tannin-Related Marker Constituents Gallic Acid, Corilagin, Chebulagic Acid, Ellagic Acid and Chebulinic Acid in Four *Terminalia* Species from India, Journal of Chromatographic Science 2014;1-8, doi:10.1093/chromsci/bmu096.
Dhingra, et al., Antiepileptic activity of ellagic acid, a naturally occurring polyphenolic compound, in mice, Journal of Functional Foods 10 (2014) 364-369, journal homepage: www.elsevier.com/locate/jff.
Eshwarappa, et al., Antioxidant Activities of Leaf Galls Extracts of *Terminalia chebula* (Gaertn.) Retz. (Combretaceae) Acta Sci. Pol. Technol. Aliment. 14(2) 2015, 97-105.
Ghosh, et al., (2017) Male contraceptive efficacy of poly herbal formulation, contracept-TM, composed of aqueous extracts of *Terminalia chebula* fruit and *Musa balbisiana* seed in rat, Pharmaceutical Biology, 55:1, 2035-2042, DOI: 10.1080/13880209.2017.1357734.
Guan, In Vitro Inhibitory Effects of Chebulinic Acid on the Contractile Responses of Cardiovascular Muscles, Clinical and Experimental Pharmacology and Physiology (1996) 23, 747-750.
Han, et al., Preparative isolation of hydrolysable tannins chebulagic acid and chebulinic acid from Terminalia chebula by high-speed counter-current chromatography, J. Sep. Sci. 2006, 29, 1653-1657.
Haynes, et al., Current Models of Human Prostate Contractility, Clinical and Experimental Pharmacology and Physiology (2005) 32, 797-804.
Jikai, et al., One Step Purification of Corilagin and Ellagic Acid from Phyllanthus urinaria using High-Speed Countercurrent Chromatography, Phytochemical Analysis, Phytochem. Anal. 13, 1-3 (2002).
Jiwrajka, et al., Drugs for benign prostatic hypertrophy, Australian Prescriber, vol. 41: No. 5: Oct. 2018.
Jung, et al., Silodosin for the treatment of lower urinary tract symptoms in men with benign prostatic hyperplasia (Protocol), Cochrane Database of Systematic Reviews, 2017, Issue 3. Art. No. CD012615.
Keehn, et al., Phytotherapy for Benign Prostatic Hyperplasia, Springer Science Business Media New York, Published May 14, 2016.
Kesharwani, et al., Anti-HSV-2 activity of *Terminalia chebula* Retz extract and its constituents, chebulagic and chebulinic acids, Kesharwani et al. BMC Complementary and Alternative Medicine (2017) 17:110.
Klika, et al., The structural and conformational analyses and antioxidant activities of chebulinic acid and its thrice-hydrolyzed derivative, 2,4-chebuloyl-β-D-glucopyranoside, isolated from the fruit of *Terminalia chebula*, Issue in Honor of Prof. Sándor Antus, ARKIVOC 2004 (vii) 83-105.
Kolla, et al., Herba Pol 2017; 63(4): 45-56, *Terminalia chebula* Retz.—an important medicinal plant, From Botanical to Medical Research, vol. 63 No. 4 2017, DOI: 10.1515/hepo-2017-0024.
Lee, et al., Hydrolysable Tannins and Related Compound having Cytotoxic Activity from the Fruits of *Terminalia chebula*, Arch. Pharm. Res. vol. 18, No. 2, pp. 118-120, 1995.
Lee, et al., Hydrolyzable tannins from the fruits of *Terminalia chebula* Retz and their α-glucosidase inhibitory activities, Photochemistry xxx (2017) 1-8, journal homepage: www.elsevier.com/locate/phytochem.
Lin, et al., Antihypertensive Activity of Corilagin and Cheb Ulinic Acid, Tannins From Lumnitzera Racemosa, Journal of Natural Products, vol. 56, No. 4, pp. 629-632, Apr. 1993.
Lin, et al., Butyrate and Propionate Protect against Diet-Induced Obesity and Regulate Gut Hormones via Free Fatty Acid Receptor 3-Independent Mechanisms, PLoS One, www.plosone.org, Apr. 2012, vol. 7, Issue 4, e35240.
Mahajan, et al., Simultaneous isolation and identification of phytoconstituents from Terminalia chebula by preparative chromatography, J. Chem. Pharm. Res., 2010, 2(5):97-103.
Manosroi, et al., Biological Activities of Phenolic Compounds and Triterpenoids from the Galls of Terminalia chebula, Chemistry & Biodiversity—vol. 10 (2013), 1448-1463.
Manosroi, et al., In vitro anti-aging activities of *Terminalia chebula* gall extract, Pharmaceutical Biology, 2010; 48(4): 469-481.
Mcconnell, et al., The Long-Term Effect of Doxazosin, Finasteride, and Combination Therapy on the Clinical Progression of Benign Prostatic Hyperplasia, The New England Journal of Medicine, Dec. 18, 2003, vol. 349, No. 25.
Mcneal, et al., Pathology of Benign Prostatic Hyperplasia, 0094-0143/90, Urologic Clinics ofNorth America—vol. 17, No. 3, Aug. 1990, 477-486.
Mcvary, et al., Sildenafil Citrate Improves Erectile Function and Urinary Symptoms in Men With Erectile Dysfunction and Lower Urinary Tract Symptoms Associated With Benign Prostatic Hyperplasia:

(56) References Cited

OTHER PUBLICATIONS

A Randomized, Double-Blind Trial, The Journal of Urology, vol. 177, 1071-1077, Mar. 2007, 1071-1077.
Mcvary, et al., Tadalafil Relieves Lower Urinary Tract Symptoms Secondary to Benign Prostatic Hyperplasia, The Journal of Urology, vol. 177, 1401-1407, Apr. 2007, 1401-1407.
Milani, et al., Lower urinary tract symptoms suggestive of benign prostatic hyperplasia: latest update on α1-adrenoceptor antagonists, 2005 BJU International, 95 Supplement 4, 29-36.
Mishra, et al., Anti-secretory and cyto-protective effects of chebulinic acid isolated from the fruits of *Terminalia chebula* on gastric ulcers, Phytomedicine 20 (2013) 506-511, Contents lists available at SciVerse ScienceDirect, journ al hom epage: www.elsevier.de/phymed.
Nam, et al., Mitigation of 2,4-dinitrofluorobenzene-induced atopic dermatitis-related symptoms by Terminalia chebula Retzius, International Journal of Medicine 28: 1013-1018, 2011.
Nonaka, et al., Anti-Aids Agents, 21: Inhibitory Effects of Tannins on HIV Reverse Transcriptase and HIV Replication in H9 Lymphocyte Cells, Journal of Natural Products, vol. 53, No. 3m pp. 587-595, May-Jun. 1998.
Park, et al., Antiviral activity and possible mode of action of ellagic acid identified in *Lagerstroemia speciosa* leaves toward human rhinoviruses, BMC Complementary and Alternative Medicine 2014, 14:171, http://www.biomedcentral.com/1472-6882/14/171.
Peng, et al., Isolation of ellagic acid from pomegranate peel extract by hydrophobic interaction chromatography using graphene oxide grafted cotton fiber adsorbent, Journal of Separation Science, www.jss-journal.com, 1-34.
Pfundstein, et al., Polyphenolic compounds in the fruits of Egyptian medicinal plants (*Terminalia bellerica, Terminalia chebula and Terminalia horrida*): Characterization, quantitation and determination of antioxidant capacities, Phytochemistry 71 (2010) 1132-1148.
Reijke, et al., Comparative efficacy of two α1-adrenoreceptor antagonists, doxazosin and alfuzosin, in patients with lower urinary tract symptoms from benign prostatic enlargement, 2004 BJU International 93, 757-762, doi:10.1111/j.1464-410X.2004.04720.x.
Saranya, et al., Preparation of Terminalia Chebula Loaded Cellulose/Chitosan Composite Films and the Evaluation of Drug Release and Antimicrobial Characteristics, IJPSR, 2016; vol. 7(4): 1471-1479.
Shanmuganathan, et al., Chebulagic acid Chebulinic acid and Gallic acid, the active principles of Triphala, inhibit TNFα induced pro-angiogenic and pro-inflammatory activities in retinal capillary endothelial cells by inhibiting p38, ERK and NFkB phosphorylation, Vascular Pharmacology, Vph(2017), doi:10.1016/j.vph.2018.04.005.
Shrivastava, et al., Various treatment options for benign prostatic hyperplasia: A current update, Journal of Mid-life Health, Jan.-Jun. 2012, vol. 3, Issue 1, pp. 10-19.
Silva, et al., Current medical treatment of lower urinary tract symptoms/BPH: do we have a standard?, xxx.co-urology.com, vol. 24, No. 1, Jan. 2014, pp. 21-28.
Sivasankar, et al., Aqueous and Alcoholic Extracts of Triphala and Their Active Compounds Chebulagic Acid and Chebulinic Acid Prevented Epithelial to Mesenchymal Transition in Retinal Pigment Epithelial Cells, by Inhibiting SMAD-3 Phosphorylation, PLOS One | DOI:10.1371/journal.pone.0120512 Mar. 20, 2015.
Skolarikos, et al., Eighteen-Month Results of a Randomized Prospective Study Comparing Transurethral Photoselective Vaporization with Transvesical Open Enucleation for Prostatic Adenomas Greater Than 80 cc, Journal of Endourology, vol. 22, No. 10, Oct. 2008, 2333-2340.
Song, et al., Chebulinic acid inhibits smooth muscle cell migration by suppressing PDGF-Rβ phosphorylation and inhibiting matrix metalloproteinase-2 expression, SCieNtifiC REPOrTS | 7: 11797 | DOI:10.1038/s41598-017-12221-w, 1-11.
Srivastav, et al., Inhibition of hyaluronidase activity of human and rat spermatozoa in vitro and antispermatogenic activity in rats in vivo by *Terminalia chebula*, a flavonoid rich plant, Reproductive Toxicology 29 (2010) 214-224.
Srivastava, et al., Isolation of ellagic acid from the aqueous extract of the roots of *Decalepis hamiltonii*: Antioxidant activity and cytoprotective effect, Food Chemistry 103 (2007) 224-233.
Tarasiuk, Aleksandra, et al., Triphala: current applications and new perspectives on the treatment of functional gastrointestinal disorders, Chinese Medicine, Dec. 1, 2018, vol. 13, Nr:1, https://cmjournal.biomedcentral.com/track/pdf/10.1186/s13020-018-0197-6.pdf.
Tasaduq, et al., Hepatocurative and antioxidant pro•le of HP-1, a polyherbal phytomedicine, Human & Experimental Toxicology (2003) 22: 639-645.
Vanella, et al., Apoptotic markers in a prostate cancer cell line: Effect of ellagic acid, Oncology Reports 30: 2804-2810, 2013.
Veni, Larvicidal and ovicidal activity of *Terminalia chebula* Retz. (Family: Combretaceae) medicinal plant extracts against Anopheles stephensi, Aedes aegypti and Celux quinquefasciatus, ResearchGate, Article in Journal of Parasitic Diseases • Dec. 2016, J Parasit Dis (Jul.-Sep. 2017) 41(3):693-702.
Vilhelmova-Ilieva, et al., Tannins as Antiviral Agents, http://dx.doi.org/10.5772/intechopen.86490.
Wang, Min, et al., Chebulinic acid derived from triphala is a promising antitumour agent in human colorectal carcinoma cell lines, BMC Complementary and Alternative Medicine, Dec. 27, 2018 BioMed Central Ltd, London, UK, vol. 18, Nr:1, pp. 1-9, http://dx.doi.org/10.1186/s12906-018-2412-5.

* cited by examiner

Percolated 5 times in
95 % ethanol (1.25 L × 5)

Macerated with distilled water
(1 L × 2 ) and filtered

Left for 24 hours

Washed 3 4 times
with distilled water

PSA Expression in Prostate Tissue and Serum of BPH Induced & Treated Rats

Tissue             Serum 54 kDa 43 kDa

NC- Normal Control
Ind- Testosterone induced BPH
Fin- Finasteride
CA- Chebulinic Acid 100 mg/kg 1-CAEF 100 mg/kg
2-CAEF 200 mg/kg
3-CAEF formulation 200 mg/kg

Prostate Weight Index and Recovery after Treatment

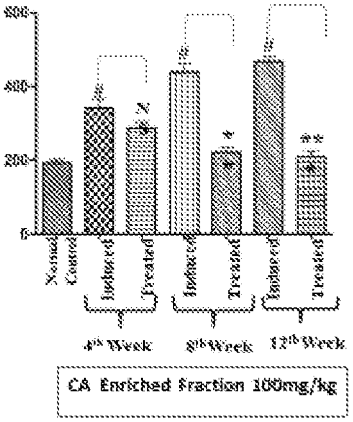

| Group | Prostate weight index (PI) |
|---|---|
| Normal control | 192.3 |
| BPH Induced after 4th week | 342.7 |
| CA enriched fraction treatment after 4th week | 287.7 |
| BPH Induced after 8th week | 438.4 |
| CA enriched fraction treatment after 8th week | 222.8 |
| BPH Induced after 12th week | 468.0 |
| CA enriched fraction treatment after 12th week | 210.7 |

| Treatment with CA enriched fraction 100mg/ kg | Prostate weight Index Recovery (%) |
|---|---|
| After 4th week | 16.04 |
| After 8th week | 49.38 |
| After 12th week | 54.98 |

Figure 6

PSA level in Serum Reduced after Treatment

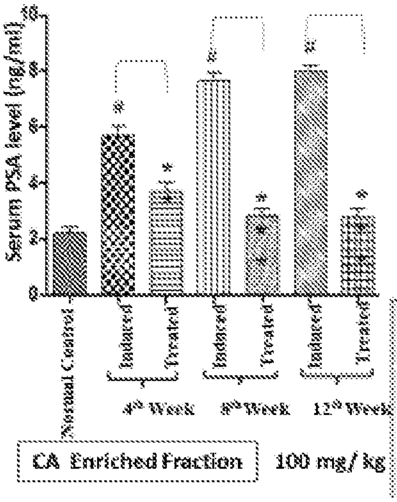

| Group | PSA level (ng/ml) |
|---|---|
| Normal control | 2.214 |
| BPH Induced after 4th week | 5.690 |
| CA enriched fraction treatment after 4th week | 3.692 |
| BPH Induced after 8th week | 7.629 |
| CA enriched fraction treatment after 8th week | 2.807 |
| BPH Induced after 8th week | 8.225 |
| CA enriched fraction treatment after 12th week | 2.658 |

| Treatment with CA enriched fraction 100 mg/ kg | PSA level inhibition (%) after Treatment |
|---|---|
| After 4th week | 35.11 |
| After 8th week | 63.20 |
| After 12th week | 67.68 |

Figure 7

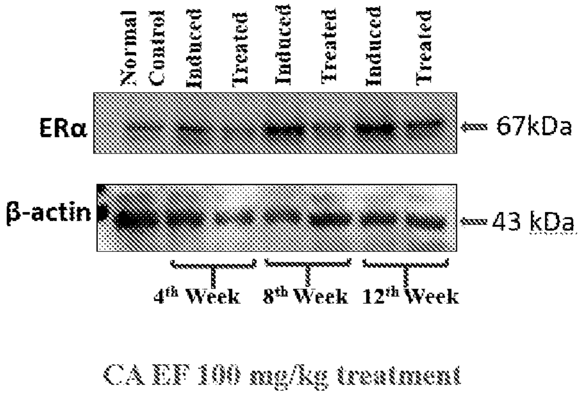
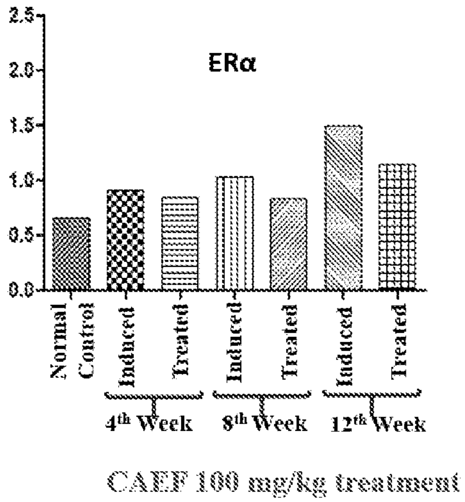
Figure 16

CHEBULINIC ACID AND ITS ENRICHED FRACTION FROM THE FRUITS OF *TERMINALIA CHEBULA* FOR TREATMENT OF BENIGN PROSTATIC HYPERPLASIA (BPH) AND ITS PREPARATION THEREOF

CROSS-REFERENCE TO RELATED PATENT APPLICATIONS

The present application is a U.S. national stage application under 35 U.S.C. § 371 of PCT/IN2021/050898, filed Sep. 13, 2021, which claims priority to Indian Patent Application number 202011039625 filed on Sep. 12, 2020. The disclosures of the aforementioned priority applications are incorporated herein by reference.

FIELD OF THE INVENTION

The present invention relates to chebulinic acid enriched fraction (CAEF) for the prevention or treatment of Benign Prostatic Hyperplasia (BPH) and its related symptoms. Particularly, present invention relates to Chebulinic acid (CA) and chebulinic acid enriched fraction (CAEF) isolated from the fruits of *Terminalia chebula* and its enriched fraction (CAEF). The present invention also relates to a method for the preparation of a standardised chebulinic acid enriched fraction (CAEF). This invention further relates to a convenient and economically viable method for the isolation of chebulinic acid (CA) and ellagic acid (EA) from the dried and powdered fruits of *T. chebula* in pure form without the use of HPLC, column chromatography or resins.

BACKGROUND OF THE INVENTION

Located anterior to the rectum, the prostate is a heart shaped, walnut-sized gland that is located below the urinary bladder surrounding the proximal portion of the urethra. It consists of canals and follicles lined with columnar epithelial cells and surrounded by a fibromuscular stroma consisting of connective tissue and smooth muscle. The prostate contributes to seminal fluid, where its secretions are important in optimizing conditions for fertilization by enhancing the viability of sperm in reproductive tract. In all mammals, the prostatic secretions are stored in the acini and released into the urethra, at ejaculation, by contraction of the prostatic (stromal) smooth muscle.

The term BPH (Benign prostatic hyperplasia) refers to a histologic condition, namely the presence of stromal glandular hyperplasia within the prostate gland. It is a progressive disease that is commonly associated with bothersome lower urinary tract symptoms (LUTS) such as frequent urination, urgency, nocturia, decreased and intermittent force of stream, and the sensation of incomplete bladder emptying. It is characterized by an unregulated proliferative process of connective tissue, smooth muscle and glandular epithelium within the prostate. In more severe stages, untreated BPH leads to complications such as urinary tract infection, acute urinary retention and ultimately, obstructive nephropathy.

BPH is one of the most common conditions in elderly men with a prevalence rate of more than 70% at 60 years old age and 90% older than 70 years. Although in most cases initiation of treatment relieves most of BPH symptoms, still urinary tract obstruction can cause major health problems such as bleeding from the prostate, recurrent infections, bladder stones, inability to urinate, kidney insufficiency or failure. Therefore, it is essential to identify and initiate effective treatment strategies in order to overcome these complicated situations in BPH patients. Although BPH is generally not a life-threatening condition, it can have a marked effect on a patient's quality of life. (see Woodard et al. *Consult Pharm* 2016; 31: 412-424, Haynes and Ventura. *Clin Exp Pharmacol Physiol* 2005; 32: 797-804, Srivastava and Gupta. *J Midlife Health.* 2012; 3: 10-19, Roehrborn *International Journal of Impotence Research* 2008; 20 Suppl 3: S11-8, Jung et al. *Cochrane Database Syst Rev* 2017; 11:CD012615, Alivizatos and Skolarikos 2008, USA: Springer, Beiraghdar et al. *Pharm Biol.* 2017; 55(1):1800-5, de Reijke and Klarskov *BJU Int* 2004; 93:757-62, McConnell et al. *New England Journal of Medicine* 2003; 349 (25):2387-98, Milani and Djavan. *BJU International* 2005; 95 Suppl 4:29-36, Yoo et al. *Korean Journal of Urology* 2012; 53(3):139-48).

BPH is defined as a disease that manifests as a lower urinary tract dysfunction due to benign hyperplasia of the prostate, usually associated with enlargement of the prostate and LUTS suggestive of lower urinary tract obstruction. Currently, there are two classes of drugs used for the treatment of BPH, i.e. $\alpha_1$-adrenergic receptor antagonists (alfuzosin, doxazosin, tamsulosin, terazosin) and 5α-reductase inhibitors (finasteride and dutasteride) (see McVary et al., *J Urol.* 2007; 177(3):1071-7, *J Urol.* 2007; 177(4): 1401-7). Besides, Combination therapy is most commonly started when BPH symptoms are refractory to monotherapy. (see Silva et al. *Curr Opin Urol* 2014; 24:21-8). Further, minimally invasive therapies (MITs) are also used for BPH treatment which usually involve heating the prostate gland by various means (electrical, microwave, laser). Insertion can be directly into the prostate via a needle or into the urethra via a catheter, probe or endoscope (see Srivastava and Gupta. *J Midlife Health.* 2012; 3).

Most of the drug treatments for BPH are associated with some side-effects. Although systemic adverse effects are less frequent with the more selective α-blockers, they increase the risk of ejaculatory dysfunction. Other adverse effects of α-blockers include retrograde ejaculation, erectile dysfunction, nasal congestion, hypotension, dizziness and tachycardia. The most common adverse effects of 5α-reductase inhibitors are erectile dysfunction, decreased libido, ejaculation and semen count. These adverse effects can be irreversible and debilitating. Further, combinations of drugs are likely to have more adverse effects than monotherapy (see Srivastava and Gupta. *J Midlife Health.* 2012; 3: 10-19, Jiwrajka et al. *Aust Prescr* 2018; 41: 150-153). Surgical methods may also affect the quality of life (Beiraghdar et al. *Pharm Biol.* 2017; 55(1):1800-5).

As an alternative therapy in BPH, phytotherapy or administering plant extracts with therapeutic purposes to manage BPH, is rapidly growing each day (Keehn et al. 2016, *Curr Urol Rep.* 17:1-6). Thus, the demand of herbal drugs for the treatment of BPH is increasing and plant-based drugs from the ayurvedic system are being explored more not only in India but globally as well.

Currently, more than 30 phytotherapeutic compounds have been used for LUTS/BPH treatment (Keehn & Lowe, 2015 *The Canadian Journal of Urology,* 22(Suppl 1), 18-23). Of these, *Serenoa repens* (saw palmetto), *Hypoxis rooperi, Secale cereale, Pygeum africanum, Urtica dioica*, and *Curcubita pepo* have been widely used and studied (Wilt et al. 2000, *Public Health Nutrition,* 3, 459-472; Suzuki et al. *Phytotherapy Research.* 2018; 1-4). But, due to lack of proper studies such as identification of biomarkers and quantity of biomarker required to show efficacy, phytotherapies are not gaining much advantage.

*Terminalia chebula* (*T. chebula*) belongs to the family of Combretaceae and commonly called as Black myrobalan. It is a medium to large-sized tree widely distributed throughout most parts of Asia. Also known as king of medicine, it is a well-recognised plant in traditional systems of medicine like Ayurveda, Siddha and Unani. It is extensively used in the preparation of several Ayurvedic formulations. Aerial parts of *T. chebula* like fruits, bark, leaves and seeds are known to be a reservoir of distinct chemical entities which are responsible for their numerous biological activities. Alcoholic, aqueous or aqueous—alcoholic extracts of various parts of *T. chebula* are known to exhibit beneficial health effects. Numerous literature reports completely validate the traditional use of *T. chebula* for ailments like tumour, microbial infections/wounds, digestive problems and much more. Based on several indigenous uses of different parts of this plant by native people, many research groups are interested in exploring the bioactive components of this plant and their activity profile thereof.

The leaves of *T. chebula* are rich source of numerous tannins and structurally diverse polyphenols. Several literature reports exist approving the traditional usage of leaf extracts. To name a few, the aqueous/alcoholic leaf extracts are known to possess antioxidant and hypoglycaemic activity, α-glucosidase inhibitory activity and larvicidal and ovicidal activity against three important vector mosquitoes. (See Arya et al., *E-Journal of Chemistry* (2012) 9: 883-892; K. Anam et al. *International Journal of Pharmacology* (2009) 5: 277-280; T. Veni et al., *J Parasit Dis* (2017) 41: 693-702).

Further, *T. chebula* seeds are also a biologically active part of this plant and exhibit biological activities. The seed extract was reported to have potential for alleviation of atopy-like symptoms (see Nam et al., *International Journal of Molecular Medicine* (2011) 28: 1013-1018). Like the leaves and the fruits, the seed extract also possess remarkable anti-microbial property (see Saranya et al., *IJPSR* (2016) 7: 1471-1479).

The pharmacological efficacy of leaf gall extracts of *T. chebula* is also described in literature. It is known to display anti-aging and antioxidant activities (see Manosroi et al., *Pharmaceutical Biology* (2010) 48: 469-481; Eshwarappa et al., *Acta Sci. Pol. Technol. Aliment.* (2015) 14: 97-105). The bark of *T. chebula* also exhibit activities like antioxidant and antibacterial (see Venkatesan et al., *Free Radicals and Antioxidants* (2017) 7: 43-49).

The most explored bioactive part of this plant is its fruits. The dried fruits contain plethora of chemical constituents like alkaloids, glycosides, flavonoids, tannins and saponins which either alone or synergistically contributes to various pharmacological actions. The fruit extract of *T. chebula* is known to display different biological properties like anticancer, anti-inflammatory, antioxidant, anti-protozoal, antimicrobial, hepato and renal protective activities, and in the management of metabolic syndrome. There are few reports showing the anti-fertility activity of *T. chebula* fruit extract. Srivastav et al. have reported the antispermatogenic activity and contraceptive efficacy of *T. chebula* extract. In another paper, Ghosh et al. have reported the male contraceptive efficacy of poly herbal formulation, contracept-TM, composed of aqueous extracts of *T. chebula* fruit and *Musa balbisiana* seed in rat. The phenolic active compounds might play vital role in the influence of biological activity (see Kolla et al. *Herba Pol.* 2017; 63(4):45-56; Srivastav et al., *Reproductive Toxicology* (2010) 29: 214-224; Ghosh et al., Pharmaceutical Biology (2017) 55: 2035-2042).

In folklore medicinal systems, many times two or more plant extracts or mixtures are used in combination to produce synergistic effect and combat many health issues. TRIPHALA, which is a combination of equal parts of dried and grinded fruits of *T. chebula, T. bellerica* and *Emblica officinalis*, is widely used to get rid of digestive issues. The powdered fruits of *T. chebula* and *T. bellerica* are reported to produce synergistic antibacterial activity (see Thirunavukkarasu et al., *Int J Curr Pharm Res.* (2017) 9: 8-11). A polyherbal formulation-HP-1 containing *T. chebula* is known to display hepatocurative and antioxidant profile. A multicomponent herbal formula Ledretan-96 containing *T. chebula* is reported to show antiviral activity (see Tasaduq et al., *Hum Exp Toxicol.* (2003) 22: 639-645; Badmaev et al., *Phytother. Res.* (2000) 14: 245-249).

Furthermore, several patents exist in literature wherein the *T. chebula* extract has been used in combination to produce purposeful biological results (US009750778B2, US20060257507A1, WO2013155175A1).

All the above-mentioned literature reports completely support the medicinal importance of *T. chebula*. It also presents the need to identify the bioactive constituents of the same in order to develop them as important herbal products. Major phytoconstituents from *T. chebula* can be categorized into four types: (a) Gallic acid and simple gallate esters like 3,4,5-tri-O-galloyl-(3R,4S,5R)-shikimic acid (see Nonaka et al., *J. Nat. Prod.*, (1990), 53, 587-595); (b) Chebulic ellagitannins like chebulic acid, chebulanin, also known as terminalic acid, chebulinic acid, chebulagic acid methyl neochebulagate, methyl neochebulinate; (c) Non-chebulic ellagitannins like corilagin, punicalagin; (d) Ellagic acid and derivatives like Gallagic acid, (S)-Flavogallonic acid. Besides some ellagic glycosides, β-sitosterol etc. is also found but only in minor amount (see Pfundstein et al., *Phytochemistry* (2010) 71: 1132-1148).

Among the chemical compounds present in *T. chebula*, two major phytoconstituents are chebulinic acid and ellagic acid. They are found in the fruits of *T. chebula* in a major quantity. Both these compounds are reported to possess remarkable bioactivities. Chebulinic acid is a major bioactive compound present in the fruits of *T. chebula*. It is a hydrolysable tannin and chemically it is 1.3,6-tri-O-galloyl-2,4-chebuloyl-beta-D-glucose. Ellagic acid, a dimeric derivative of gallic acid, is generated by the hydrolysable ellagitannins. Chemically it is 2,3,7,8-tetrahydroxy[1]benzopyranol[5,4,3-cde]benzopyran-5,10-dione found in a wide variety of dietary sources like several berries, pomegranate and walnut.

Chebulinic acid (CA), depicted in the compound of formula (1), is well known polyphenolic compound that display promising activities towards various diseases. A wide range of biological activities of CA is reported in literature. CA is reported to exhibit activities like antihypertensive, angiogenesis inhibitor, antiviral activity against HSV-2, antiatherogenic effects, cardiovascular effects, anti-secretory and cyto-protective, antioxidant, prooxidant action, proangiogenic and pro-inflammatory, antibacterial and most importantly anti-cancer (see Lin et al., *Journal of Natural Products* (1993) 56: 629-632; Lu et al., *PLoS ONE* (2012) 7: e43934; Kesharwani et al., *BMC Complementary and Alternative Medicine* (2017) 17:110; Song et al., *Scientific Reports* (2017) 7: 11797; Guan et al., *Clinical and Experimental Pharmacology and Physiology* (1996) 23: 747-750; Mishra et al., Phytomedicine (2013) 20:506— 511; Klika et al., *ARKIVOC* (2004) (vii): 83-105; Yi et al., *Toxicology in Vitro* (2009) 23: 425-431; Shanmuganathan et al., *Vascul Pharmacol.* (2018) 108: 23-35; Vu et al., *PLoS ONE* (2017)

12: e0181499; Chhabra et al., *Phytother. Res.* (2017) 31: 1849-1857; Yi et al., *Acta Pharmacol Sin.* (2004) 25: 231-8). CA is also reported to be a potential candidate for Proliferative Vitreoretinopathy (PVR) disease management and reduction of Glutamate-induced excitotoxicity and oxidative stress (see Sivasankar et al., *PLoS ONE* (2015) 10: e0120512; Song et al., *Bioorg. Med. Chem. Lett.* (2017) 28: 249-253). CA is also reported to be a potential candidate for Proliferative Vitreoretinopathy (PVR) disease management and reduction of Glutamate-induced excitotoxicity and oxidative stress (see Sivasankar et al., *PLoS ONE* (2015) 10: e0120512; Song et al., *Bioorg. Med. Chem. Lett.* (2017) 28: 249-253.

(1)

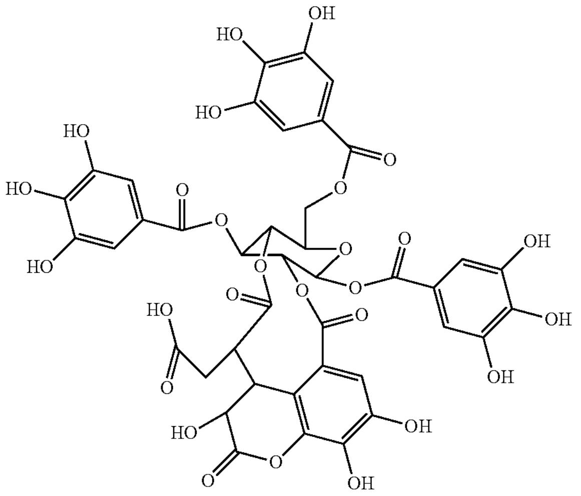

Chebulinic acid (2)

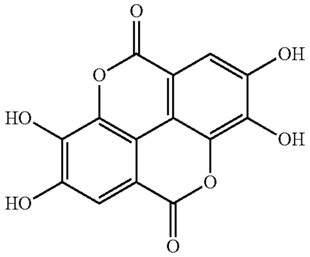

Ellagic acid

Likewise, ellagic acid, depicted in the compound of formula (2), is another active compound found in *T. chebula*. It is a naturally occurring polyphenolic compound having several potential pharmacological properties mainly associated with its ability to modulate the cell redox changes. For e.g. ellagic acid is proven to possess remarkable anti-cancer property (see Zahin et al., *BioMed Research International*, (2014): 467465; Vanella et al., *Oncol. Rep.* (2013) 30: 2804-2810). In addition, ellagic acid also possess bioactivities like antimicrobial and immunomodulating activities (Abuelsaad et al., *Life Sci.* (2013) 93: 714-722; antiviral activity (Park et al., *BMC Complement Altern. Med.* (2014) 14: 171); anti-epileptic activity (Dhingra et al., *J. Funct. Foods* (2014) 10: 364-369).

As evidenced by the extensive and significant pharmacological activity of the bioactive constituents i.e., chebulinic acid (CA) and ellagic acid (EA) obtained from *T. chebula*, there is a need to develop a process to isolate these bioactive compounds with high level purity and in quantity, up to the maximum possible extent in an extract of these plants. In one embodiment, the present invention accompanies a highly cost-effective and sustainable process for the large-scale isolation of chebulinic acid (CA) and ellagic acid (EA).

Although, the literature reports approve the therapeutic potential of chebulinic acid (CA), most of the studies are in vitro or just at a primary stage hence need further validation. Since in vivo or the animal studies require large quantity of chebulinic acid (CA) which is tedious as well as expensive to isolate at a substantial scale. The reported isolation processes involve the use of HPLC, reverse phase silica gel or resins and are mainly employed for minute scale isolation.

Some research groups successfully isolated pure chebulinic acid (CA) with the help of advanced chromatography techniques like HPLC but the isolated quantity was marginally low as compared to its total quantity present in the plant sample. One research group have isolated 34 mg of chebulinic acid (CA) from 600 g dried and powdered fruits using Sephadex LH-20, Lichroprep RP-18 and MCI-gel CHP 20P columns (see Lee et al., *Arch. Pharm. Res.* (1995) 18: 118-120). Another group have carried out the isolation of 141 mg of chebulinic acid using preparative RP-HPLC from 200 g of powdered fruit (Klika et al., *ARKIVOC* (2004) (vii): 83-105). There is another report of preparative isolation of 15.8 mg of chebulinic acid (CA) with 4 g of dried fruit powder using modified High-speed counter-current chromatography (HSCCC) (see Han et al., *J. Sep. Sci.* (2006) 29: 1653-1657). A reversed-phase preparative HPLC method with UV spectrophotometric detection was used by another research group to isolate chebulinic acid (see Mahajan et al., *J. Chem. Pharm. Res.* (2010) 2: 97-103). Another research group have done successive column chromatography (CC) on Diaion HP-20, octadecyl silica gel (ODS), silica gel (SiO2), and Sephadex LH-20 columns to isolate 83 mg of pure chebulinic acid from 100 g of dry powder (see Manosroi et al., *Chem Biodivers.* (2013) 10:1448-63). A research group have developed a rapid HPLC-PDA method for identification and quantification of chebulinic acid (see Dhanani et al., *Journal of Chromatographic Science* (2015) 53:625-632). An ultrasound assisted extraction and high-speed counter-current chromatography was also used to isolate 18 mg of chebulinic acid from 200 mg of crude sample (see Zou et al., *J. Sep. Sci.* (2016) 39: 1278-1285). Another group also reported isolation by using ODS C18 MPLC column, Sephadex LH-20 column along with semi-preparative HPLC column to isolate 10 g of chebulinic acid from 1.8 kg fruits (see Lee et al., *Phytochemistry* (2017) 137: 109-116).

Although ellagic acid (EA) is found to be present in several plant species, its large-scale isolation is way more difficult. Previously, High-Speed Counter current Chromatography (HSCCC) has been successfully applied to the preparative separation of corilagin and ellagic acid in one step from the Chinese medicinal plant *Phyllanthus urinaria* L. (see Jikai et al., *Phytochem. Anal.* (2002) 13: 1-3). Ellagic acid (EA) was isolated from the aqueous extract of the roots of *Decalepis hamiltonii* using LH-20 column and HPLC (see Srivastava et al., *Food Chemistry* (2007) 103: 224-233). Further, Ellagic acid was isolated from pomegranate peel extract by hydrophobic interaction using graphene oxide grafted cotton fiber as a stationary adsorbent (see Peng et al., *J Sep Sci* (2018) 41: 747-755).

Although processes for the isolation of chebulinic acid (CA) and ellagic acid (EA) has been described, but they are extremely time-consuming, involve multiple steps and are not economically viable for the large-scale isolation in substantially pure form that could be suitable for its pharmaceutical application. It is evident that there is an urgent need to develop a method for quantitative scale isolation of chebulinic acid (CA) and ellagic acid (EA).

Besides, it would also be beneficial to provide an efficient and easy process for the preparation of standard fraction enriched with therapeutically important polyphenol from *T. chebula*.

Herein, we successfully identified a novel, convenient, easy and cost-effective process for the preparation of chebulinic acid enriched fraction (CAEF). We also investigated its effect in the management of BPH and found it to be very effective. Further, we also developed a novel, easy and cost-effective process for the large-scale isolation of CA and EA without tedious and expensive column chromatography and HPLC with remarkable purity.

OBJECTS OF THE INVENTION

Main objective of the present invention is to provide chebulinic acid (CA) enriched fraction for the prevention or treatment of Benign Prostatic Hyperplasia (BPH) and its related symptoms.

Another object of the invention is to develop a reliable process for the preparation of a standardised enriched fraction with >50% of chebulinic acid (CA).

Yet another object of the invention is to standardize the dose range to show beneficial effect of chebulinic acid (CA) enriched fraction for the management of BPH.

Still another objective of the present invention is to develop an optimized extraction, fractionation process to isolate pure chebulinic acid (CA) and ellagic acid (EA) from the dried fruits of *T. chebula* without using any chromatographic techniques.

SUMMARY OF THE INVENTION

Accordingly, present invention provides a chebulinic acid enriched fraction [CAEF] comprising:

i. chebulinic acid in the range of 50 to 80%;
ii. ellagic acid [EA] in the range of 5 to 10%.
iii. a phenolic compound [tannins] in the range of 10 to 45%.

In an embodiment of the present invention, said fraction is useful for treatment of prostatic hyperplasia considerably without affecting histological indices.

In another embodiment, present invention provides a process for the isolation and purification of CA enriched fraction [CAEF] comprising the steps of:

a) grinding fruit of *Terminalia chebula* plant to provide a powder;
b) extracting the powder as obtained in step (a) with 6.5 L of 95% solvent to provide an extract;
c) drying the extract as obtained in step (b) to obtain a powder;
d) macerating the powder as obtained in step (c) with water and leaving for 48 to 50 hrs at room temperature in the range of 20 to 30° C. followed by filtration to give Chebulinic Acid Enriched Fraction [CAEF];
e) washing the CAEF with water to obtain chebulinic acid (CA) and water insoluble extract;
f) washing water insoluble extract as obtained in step (e) with acetone to obtain Ellagic acid [EA].

In yet an embodiment of the present invention, solvent used is selected from ethanol or methanol.

In yet an embodiment of the present invention, yield of the CA is in the range of 10 to 15% with purity in the range of 95 to 98%.

In yet an embodiment of the present invention, the process for the preparation of CAEF from the fruits of *T. chebula* in which CA quantity will be more than 50%.

In yet another embodiment, present invention provides a formulation comprising:

i. chebulinic acid enriched fraction [CAEF] in the range of 50 to 80%;
ii. a pharmaceutically acceptable excipients, adjuvants, solvents, carriers, flavours, colouring or coatings either alone or combination in the range of 20 to 50%.

In yet an embodiment of the present invention, said formulation suppressed the development of prostatic hyperplasia considerably without affecting histological indices.

In yet an embodiment of the present invention, said formulation administered orally in capsule, caplet, tablet or syrup dosage forms.

In yet another embodiment, present invention provides a use of a formulation for the treatment and management of benign prostatic hyperplasia.

In still another embodiment of the present invention, there is provided a method of treating or preventing benign prostatic hyperplasia in a subject comprising administering an effective amount of a formulation comprising chebulinic acid enriched fraction [CAEF] and a pharmaceutically acceptable excipients, adjuvants, solvents, carriers, flavours, colouring or coatings either alone or combination.

Prostate Weight Index of treated groups, received the oral doses of Finasteride (Positive Control), 100 mg/kg of Chebulinic acid and 100 & 200 mg/kg Chebulinic acid Enriched Fraction (CAEF) as well as 200 mg/kg of its formulation. The data are presented as the mean±standard error of the mean of n=5 (#P<0.001 for Control group Vs. Induced group; ***P<0.001 for Induced group Vs. BPH treated group).

Figure 4:
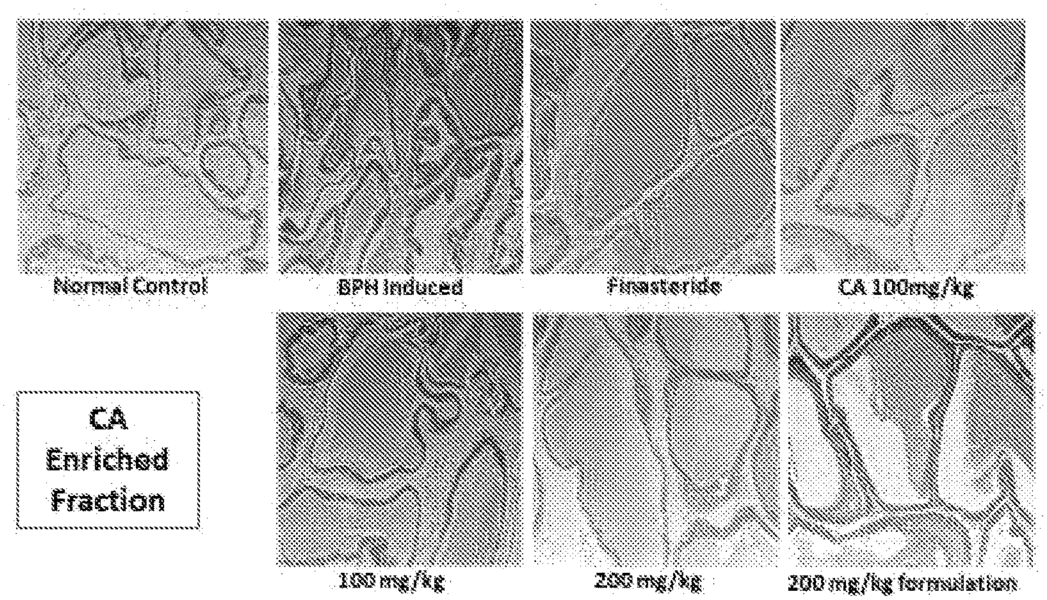

FIG. 4 represents histopathological studies of prostate with the treatment of chebulinic acid (CA) and chebulinic acid enriched fraction (CAEF) obtained from *T. chebula* fruits for the management of BPH.

Effect of Chebulinic acid (CA) & CA enriched fraction (CAEF) was observed on histological changes of prostatic tissues in testosterone induced BPH rats (After 28 days). Representative H&E histology of prostate sections from Testosterone-induced BPH rats (magnification, ×100) indicating prostatic hyperplasia Changes for the Control, Testosterone-induced BPH, Finasteride, CA (100 mg/kg) treated and CAEF (100 & 200 mg/kg) treated groups. Treatment with CAEF considerably decreased the epithelial thickness of the prostate as compared to the Testosterone induced group and also increased the prostatic lumen significantly in 200 mg/kg of CAEF treated animals.

Figure 5:
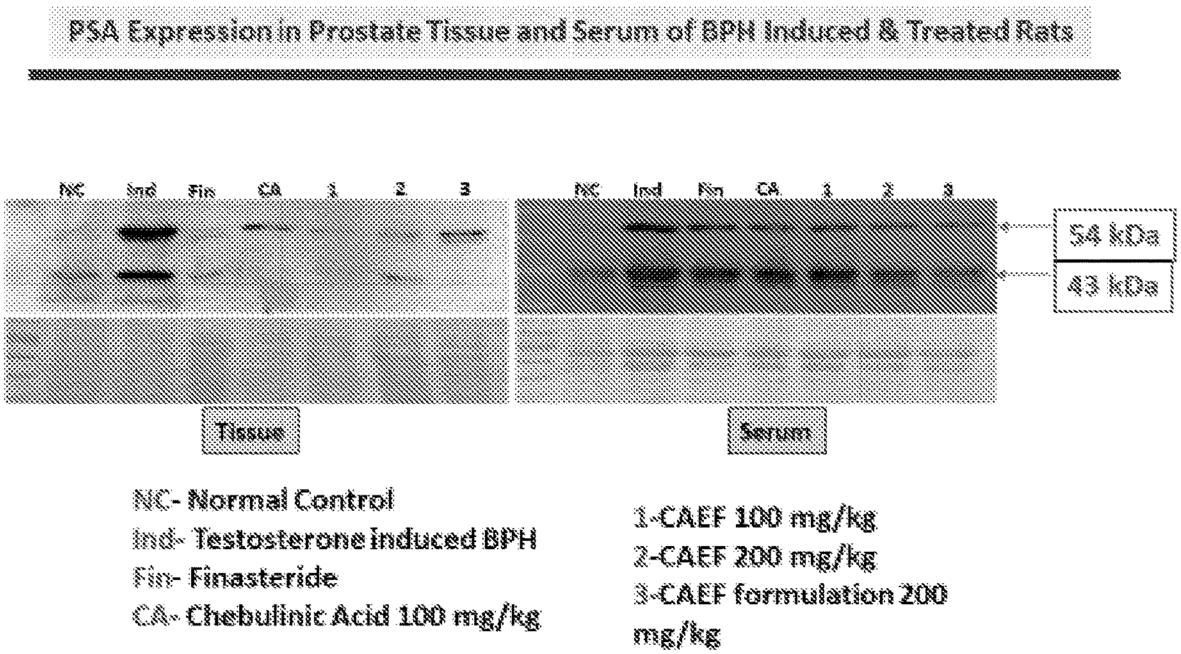

FIG. 5 represents PSA expression in prostate tissue and Serum; after the treatment of chebulinic acid (CA) and chebulinic acid enriched fraction (CAEF) obtained from *T. chebula* fruits for the management of BPH within three weeks.

Expressions of Prostate-Specific Antigen (PSA) in prostate tissue as well as in serum of treated rats was found to be down-regulated after the treatment. Representative western blot analysis showed quite similar effect of CA (100 mg/kg) as well as CAEF (200 mg/kg) and CAEF formulation (200 mg/kg).

FIG. 6 represents Prostate weight index with the treatment of 100 mg/kg b.w dose of chebulinic acid enriched fraction (CAEF) obtained from *T. chebula* fruits for the management of BPH for 4, 8 and 12 weeks. PI analysis showed a significant reduction in prostate size, within $8^{th}$ to $12^{th}$ week of treatment.

FIG. 7 represents PSA levels in serum, after the treatment of 100 mg/kg b.w dose of chebulinic acid enriched fraction (CAEF) obtained from *T. chebula* fruits for the management of BPH within 4, 8 and 12 weeks.

PSA level analysis in serum through ELISA in BPH induced Vs. treated groups after $4^{th}$, $8^{th}$ and $12^{th}$ week of treatment with CAEF showed significant decrease in PSA levels within $8^{th}$ to $12^{th}$ week of treatment.

Figure 8:
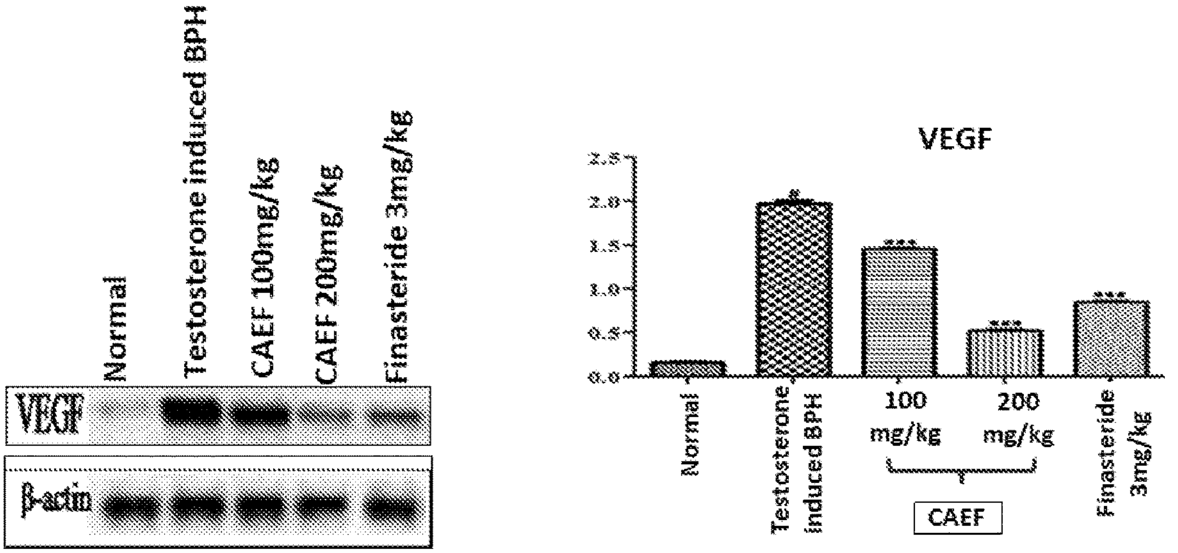

FIG. 8 represents Expression of Vascular endothelial growth factor (VEGF) in CAEF treated BPH induced Rat model within three weeks.

Vascular endothelial growth factor (VEGF) is a potent angiogenic factor, usually up-regulated in many tumors and its contribution to tumor angiogenesis is well defined. Expression of VEGF was highly upregulated in BPH induced group as compared to the normal control animals. Whereas, VEGF expression in the treated animals showed a significant reduction as compared to non-treated induced BPH group. Positive control finasteride group also showed a reduced expression of VEGF.

Figure 9:
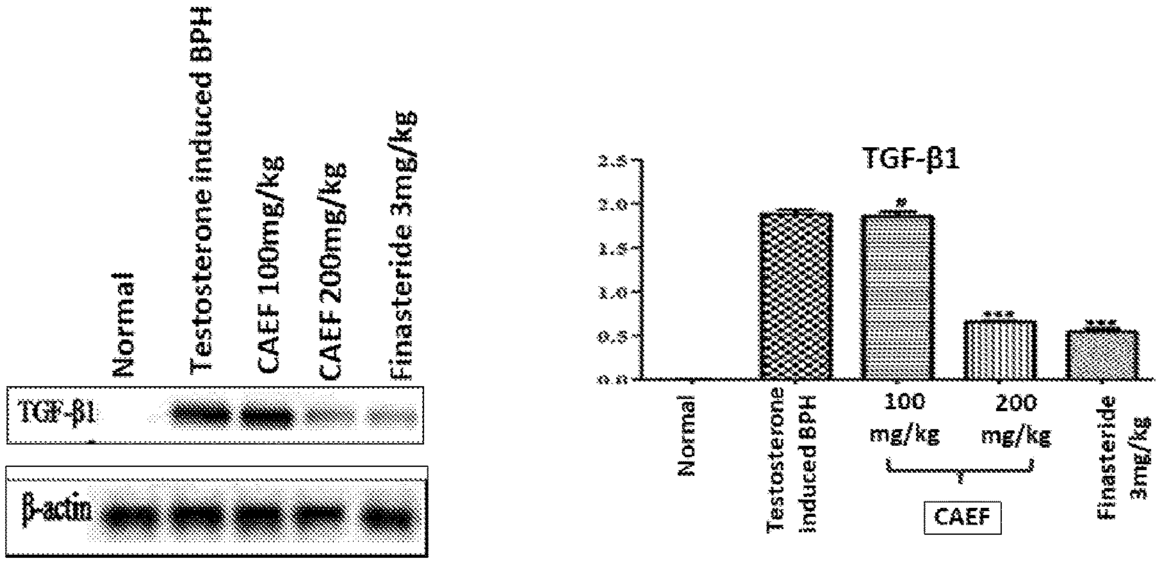

FIG. 9 represents Expression of Transforming Growth Factor Beta1 (TGF-β1). TGFβ-1 protein triggers chemical signals to regulate various cell activities inside the cell; including the growth and division (proliferation) of the cells, maturation of cells to carry out specific functions (differentiation), cell movement (motility), and controlled cell death (apoptosis).

Treatment of BPH induced animals showed a significant reduction in the expression of TGFβ-1 as compared to non-treated induced BPH group at 200 mg/kg CAEF.

Figure 10:
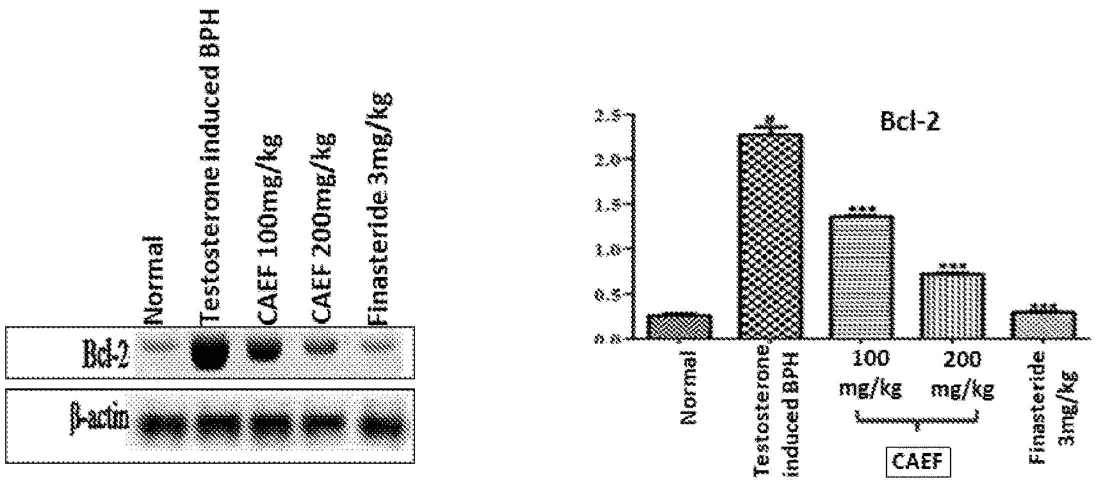

FIG. 10 represents Expression of B-cell lymphoma 2 (BCL-2). BCL-2 inhibits apoptosis by increasing the time-to-death and intrinsic cell-to-cell variations in the mitochondrial pathway of cell death. Hence, significantly reduced expression of BCL-2 in treated animals as compared to the testosterone induced BPH group, reflects increased Apoptosis in their Prostate tissue.

Figure 11:
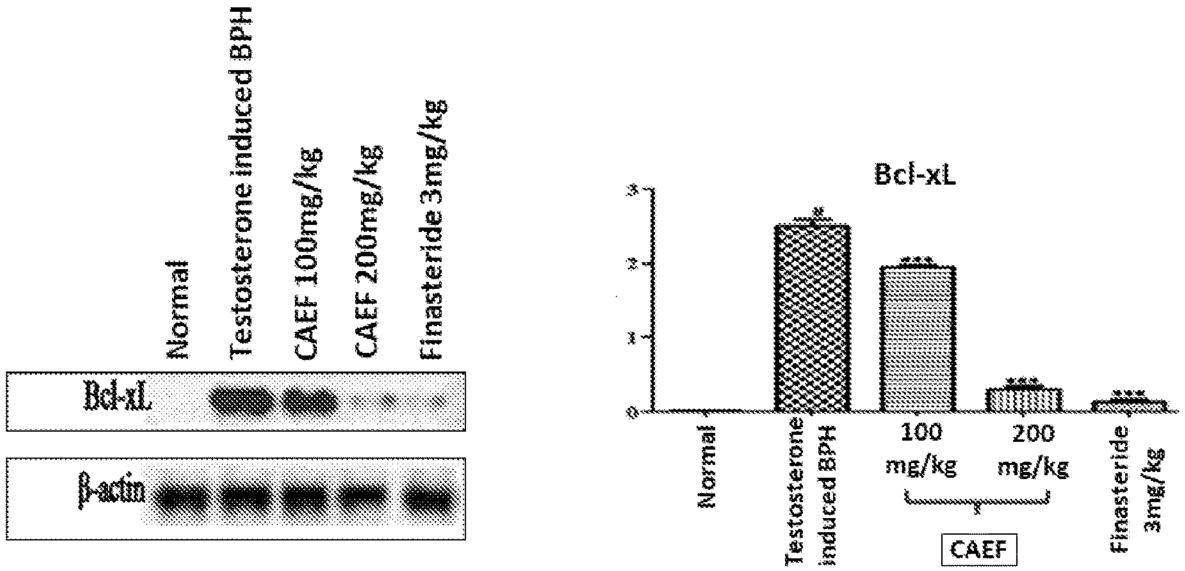

FIG. 11 represents Expression of B-cell lymphoma-extra large (Bcl-xL). Bcl-xL is a member of the Bcl-2 family of proteins, and acts as an anti-apoptotic (proliferative) protein by preventing the release of mitochondrial contents such as cytochrome c, which leads to caspase activation and ultimately, programmed cell death. A significant reduction was observed in the expression of Bcl-xL for the treated animals of 200 mg/kg CAEF as compared to non-treated induced BPH group. Finasteride treated group also showed similar reduction in the Bcl-xL expression.

Figure 12:
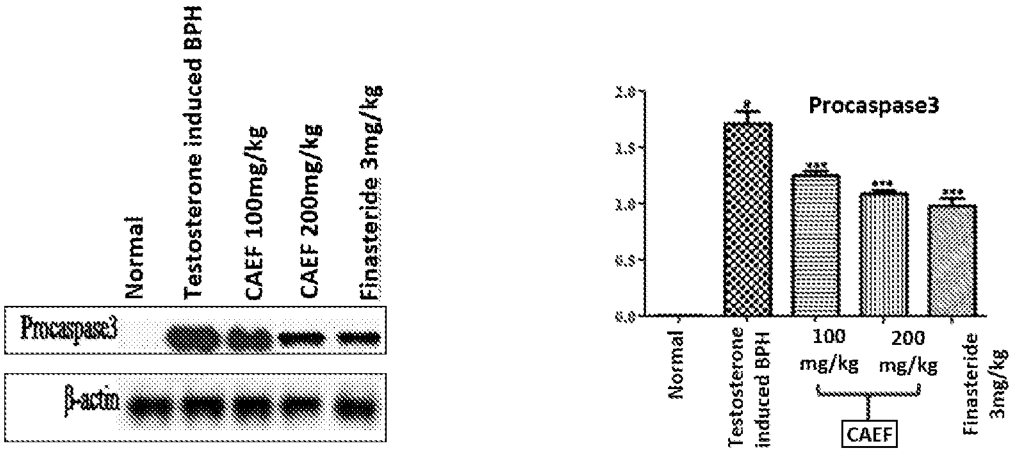

FIG. 12 represents Expression of Procaspase 3 in CAEF treated BPH Animals. Procaspase3 activates caspase-3, which interact with other caspase protein that ultimately leads to apoptosis. BPH treated animals exhibited a significant reduction in the expression of Procaspase 3 as compared to the induced animal model. Positive control finasteride group also showed a decreased expression of Procaspase3 as that of BPH induced animals.

Figure 13:
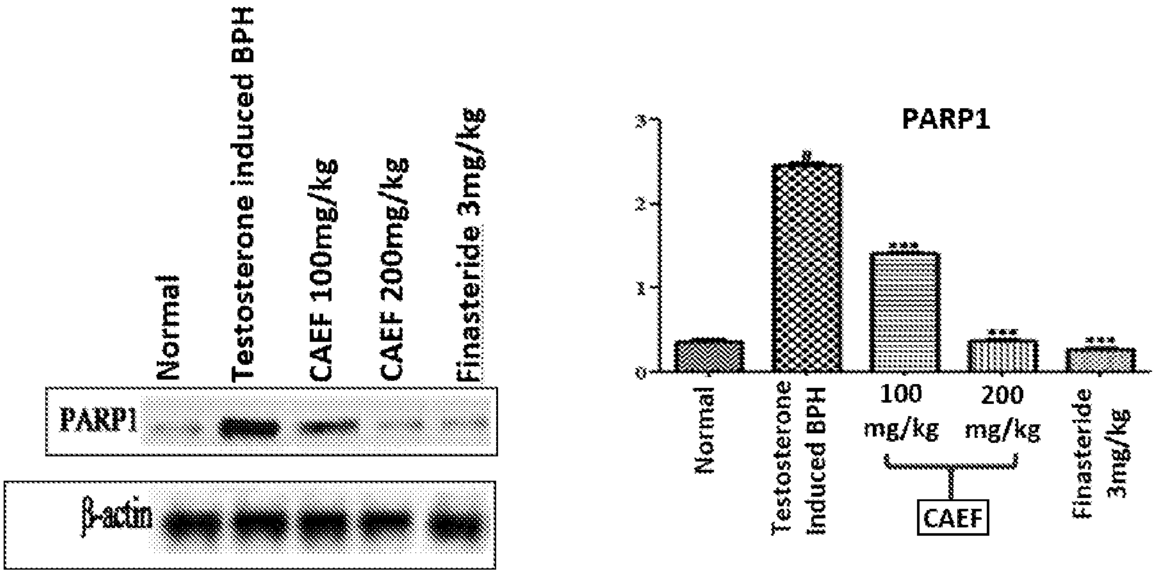

FIG. 13 represents Expression of Poly [ADP-ribose] polymerase 1 (PARP1). Poly (ADP-ribose) polymerase-1 (PARP1) is an enzyme that catalyzes the covalent attachment of polymers of ADP-ribose (PAR) moieties on itself and its target proteins. PARP enzymes are normally involved in a pathway to help damaged DNA repair inside cells. Hence, the activity of PARP1 is well documented in various cancers and the role of PARP1 is well determined in cell survival. Expression of PARP1 was significantly reduced in the treatment group as compared to BPH induced group. Positive control finasteride group also showed a reduced expression of PARP1 as that of BPH induced animals.

Figure 14:
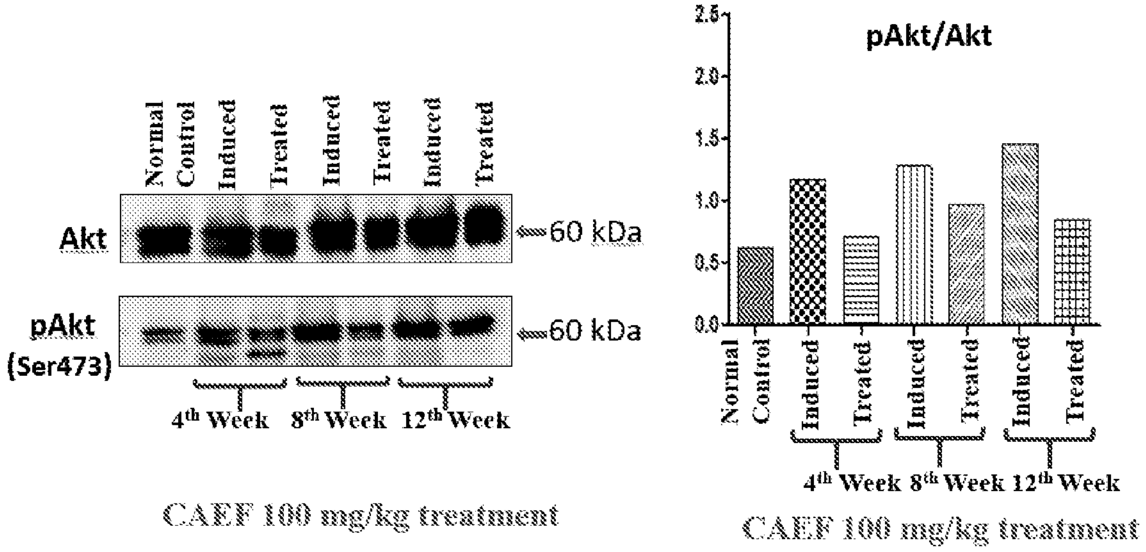

FIG. 14 represent effect of CAEF Treatment on the ratio of pAkt/Akt in Prostate Tissues. Reduced ratio of p-Akt/Akt in the treated groups reflected increased cell death through the activation of pro-apoptotic proteins.

Figure 15:
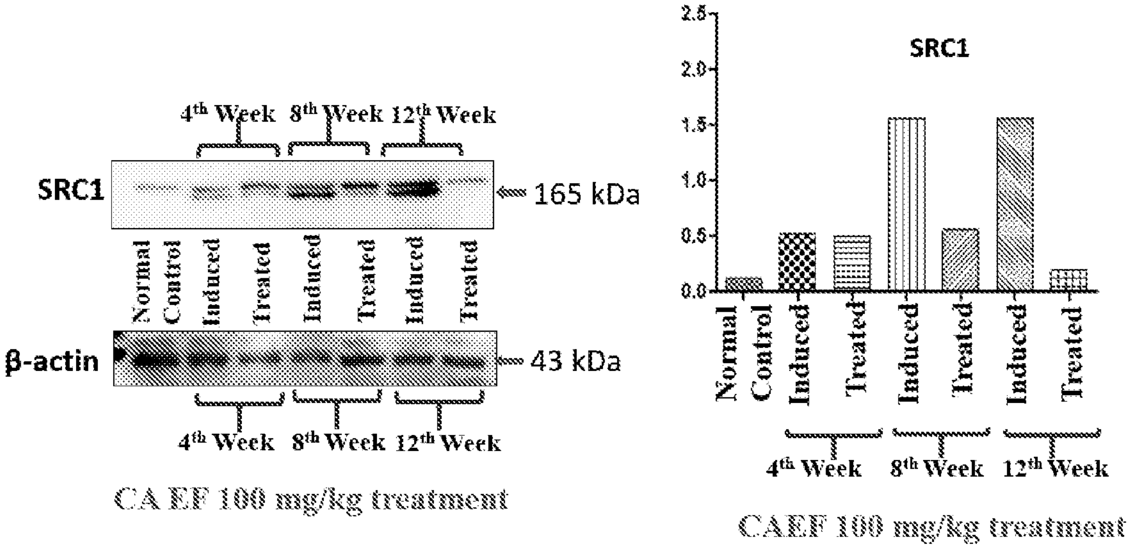

FIG. 15 represents effect of CAEF Treatment on the Expression Level of Steroid Receptor Coactivator-1 (SRC1) in Prostate Tissues. CAEF treatment down-regulates expression of SRC1 and subsequently reduce the downstream transcriptional activity of Androgen Receptor.

FIG. 16 represents effect of CAEF Treatment on the Expression Level of ERα in Prostate Tissues. Estrogen receptors (ERs) regulate cellular proliferation and differentiation thus reduction in ER-α expression showed inhibition in proliferation and increased apoptosis.

DETAIL OF THE BIOLOGICAL MATERIAL USED

The plant material is procured from local market in Lucknow (Kanhaiya Lal Ashok Kumar, Nehru Cross Chauraha, Yahiyaganj Market, Yahiyaganj, Lucknow, Uttar Pradesh, 226004).

DETAILED DESCRIPTION OF THE INVENTION

The present invention discloses chebulinic acid (CA) enriched fraction for the management of Benign Prostatic Hyperplasia and development of chebulinic acid standardized fraction (CAEF) with beneficial effect in BPH management and also development of a process for the purification of chebulinic acid (CA) and ellagic acid (EA) without any column chromatography techniques such as HPLC, CC, resins etc.

Purification of Chebulinic Acid (CA), Ellagic Acid (EA) and Preparation of Chebulinic Acid Enriched Fraction (CAEF)

To develop any natural product as a lead candidate or its standardised fraction for phytopharmaceutical drug, extensive studies needs to be performed. Multiple bioassay required to generate supportive data, which increases the demand for large scale availability of natural products. This need can be fulfilled in two ways, either by carrying out the total synthesis of required natural product in quantitative yield using cheap solvents/easy methodology or by developing a cost-effective process for isolation of natural product in high purity and preparation of the standardized fraction.

*T. chebula* contains several bioactive components, including chebulagic acid, chebulinic acid (CA), chebulic acid, ellagic acid (EA) and other low molecular weight hydrolyzable tannoids (LMWHTs). Present invention provides a method to obtain a standardised chebulinic acid enriched fraction (CAEF) for the management of BPH.

Present invention provides a process for the preparation of a standardised chebulinic acid enriched fraction (CAEF) from the dried and powdered fruits of *T. chebula* is provided.

Present invention provides a process for the large-scale isolation of chebulinic acid (CA) from *T. chebula* is provided.

Further, a process for the large-scale isolation of ellagic acid (EA) from *T. chebula* is provided.

Present invention also provides a method to obtain substantially pure chebulinic acid (CA) and ellagic acid (EA) in bulk amount.

The employed process for the purification of CA involves the following steps:

a) grinding 1 kg of fruit of *Terminalia chebula* plant to provide a powder;
b) extracting the *T. chebula* fruit powder with 6.5 L of 95% ethanol or methanol to provide ethanolic/methanolic extract;
c) drying the ethanolic/methanolic extract to give powder (400 gms);
d) macerating the resultant powder with distilled water (2 L); and
e) filtering water extract after two days and washing with distilled water (1 L) to give 50 grams of chebulinic acid (CA).

The employed process for the purification of EA involves the following steps:

a) grinding 1 kg of fruit of *Terminalia chebula* plant to provide a powder;
b) extracting the *T. chebula* fruit powder with 6.5 L of 95% ethanol or methanol to provide ethanolic/methanolic extract;
c) drying the ethanolic/methanolic extract to provide powder (400 gms);
d) macerating with the resultant powder with distilled water (2 L); and
e) washing water insoluble extract with acetone (1 L) to give 4 grams of EA.

The employed process for the preparation of chebulinic acid enriched fraction (CAEF) involves the following steps:

a) grinding the 1 kg of fruit of *Terminalia chebula* plant to provide a powder;
b) extracting the fruit powder with 6.5 L of 95% ethanol or methanol to provide ethanolic/methanolic extract;
c) drying the ethanolic/methanolic extract to provide a powder (400 gms);
d) macerating the resultant powder with distilled water (2 L); and
e) filtering water extract after two days to give CA enriched fraction (57 grams)

EXAMPLES

The following examples are given by way of illustration of the present invention and therefore these should not be construed to limit the scope of the present invention.

Example 1-3: Preparation of CAEF

Example 1

The dried fruits (1 kg) of *Terminalia chebula* were powdered and subjected to extraction process with ethanol/methanol to provide ethanolic or methanolic extract. The resultant dried extract 400 g was macerated with distilled water (2 L) and filtering the water extract after two days and washing with acetone followed by distilled water gives 50 grams of Chebulinic acid.

Example 2

The dried fruits (1 kg) of *Terminalia chebula* were powdered and subjected to extraction process with ethanol/methanol to provide ethanolic or methanolic extract. The resultant dried extract 400 g was macerated with distilled water (2 L) and filtering the water extract. The water insoluble residue was washed with acetone for 5 to 6 times resulted in 4 grams of Ellagic acid.

Example 3

The dried fruits (1 kg) of *Terminalia chebula* were powdered and subjected to extraction process with ethanol/methanol to provide ethanolic or methanolic extract. The resultant dried extract 400 g was macerated with distilled water (2 L) and filtering the water extract after two days and washing with distilled water gives 57 grams of Chebulinic acid.

Development of Self-Nanoemulsifying Drug Delivery System (SNEDDS) Formulation for Chebulinic Acid Enriched Fraction

Example 4

The SNEDDS formulation was prepared by dissolving weighed quantity of chebulinic acid enriched fraction (4% W/W) in the mixture of oleic acid (10% W/W), tween 80 (10% W/W), span 80 (80% W/W), cremophor EL (10% W/W), propylene glycol (10% W/W). This mixture was kept on stirring at 40° C. 12 h to obtain a clear and transparent preparation. This formulation was stored at ambient temperature for further use.

Results: The formed SNEEDS formulation was subjected to particle size, polydispersity index (PDI) and zeta potential analysis. Formulation showed 320.0±6.4 nm, 0.45±0.07 and −29.3±4.5 mV in mean emulsion droplet size, PDI and zeta potential respectively. The entrapment efficiency (EE) was determined by using UV-Vis spectrophotometer and it was found to 78.0±2.9%.

Example 5

The SNEDDS formulation was prepared by dissolving weighed quantity of chebulinic acid enriched fraction (4% W/W) in the mixture of oleic acid (10% W/W), tween 80 (15% W/W), span 80 (70% W/W), cremophor EL (15% W/W), propylene glycol (10% W/W). This mixture was kept on stirring at 40° C. 12 h to obtain a clear and transparent preparation. This formulation was stored at ambient temperature for further use.

Results: Particle size, PDI and zeta potential analysis of the formed SNEEDS formulation was analyzed. SNEDDS showed 380.3±5.0 nm, 0.53±0.03 and −28.9±4.8 mV in mean emulsion droplet size, PDI and zeta potential respectively. The EE was found to be 82.44±5.1%.

Example 6

The SNEDDS formulation was prepared by dissolving weighed quantity of chebulinic acid enriched fraction (4% W/W) in the mixture of oleic acid (10% W/W), tween 80 (30% W/W), span 80 (40% W/W), cremophor EL (30%

W/W), propylene glycol (10% W/W). This mixture was kept on stirring at 40° C. 12 h to obtain a clear and transparent preparation. This formulation was stored at 25° C. for further use.

Results: The formed SNEEDS formulation was subjected to particle size, PDI and zeta potential analysis. Formulation showed 280±2.9 nm, 0.37±0.04 and −25.6±6.2 mV in mean emulsion droplet size, PDI and zeta potential respectively. The EE was found to be 83.77±3.7%.

Example 7

The SNEDDS formulation was prepared by dissolving weighed quantity of chebulinic acid enriched fraction (4% W/W) in the mixture of oleic acid (10% W/W), tween 80 (35% W/W), span 80 (30% W/W), cremophor EL (35% W/W), propylene glycol (10% W/W). This mixture was kept on stirring at 40° C. 12 h. This formulation was stored at 25° C. temperature for further use.

Results: The formed SNEEDS formulation was subjected to particle size, PDI and zeta potential analysis. Formulation showed 312±3.7 nm, 0.39±0.05 and −27.0±4.4 mV in mean emulsion droplet size, PDI and zeta potential respectively. The EE was found to be 90.2±2.7%.

Example 8

The SNEDDS formulation was prepared by dissolving weighed quantity of chebulinic acid enriched fraction (4% W/W) in the mixture of oleic acid (10% W/W), tween 80 (20% W/W), span 80 (10% W/W), cremophor EL (70% W/W), propylene glycol (10% W/W). This mixture was kept on stirring at 40° C. overnight to obtain a clear and transparent preparation. This formulation was stored at ambient temperature for further use.

Results: The formed SNEEDS formulation was subjected to particle size, PDI and zeta potential analysis. Formulation showed 150±5.6 nm, 0.31±0.04 and −30.4±3.4 mV in mean emulsion droplet size, PDI and zeta potential respectively. The EE was found to be 89.76±3.5%.

Example 9

The SNEDDS formulation was prepared by dissolving weighed quantity of chebulinic acid enriched fraction (4% W/W) in the mixture of oleic acid (10% W/W), tween 80 (70% W/W), span 80 (10% W/W), cremophor EL (20% W/W), propylene glycol (10% W/W). This mixture was kept on stirring at 40° C. overnight to obtain a clear and transparent preparation. This formulation was stored at ambient temperature for further use.

Results: The formed SNEEDS formulation was subjected to particle size, PDI and zeta potential analysis. Formulation showed 86±4.6 nm, 0.23±0.05 and −27.9±5.6 mV in mean emulsion droplet size, PDI and zeta potential respectively. The EE was found to be 98.56±2.6%.

Studies of Chebulinic Acid and Its Enriched Fraction for the BPH Management in Rat Model Induced Animal Model 12-14-week-old (3 month) male Sprague-Dawley (SD) rats with initial body weights of 200-220 g were taken from National Animal Laboratory Centre, CSIR-Central drug research institute (CDRI), Lucknow. The animals were maintained in conditions in accordance with the rules and regulation of animal ethical committee. These rats were housed in a pathogen-free room at 23±2° C. and a relative humidity of 70% with an alternating 12 h light/dark cycle.

Experimental Designs

Establishment of Animal Model for Benign Prostatic Hyperplasia and Therapeutic Effect of Chebulinic Acid (CA)/Chebulinic Acid Enriched Fraction (CAEF)

Figure 1:
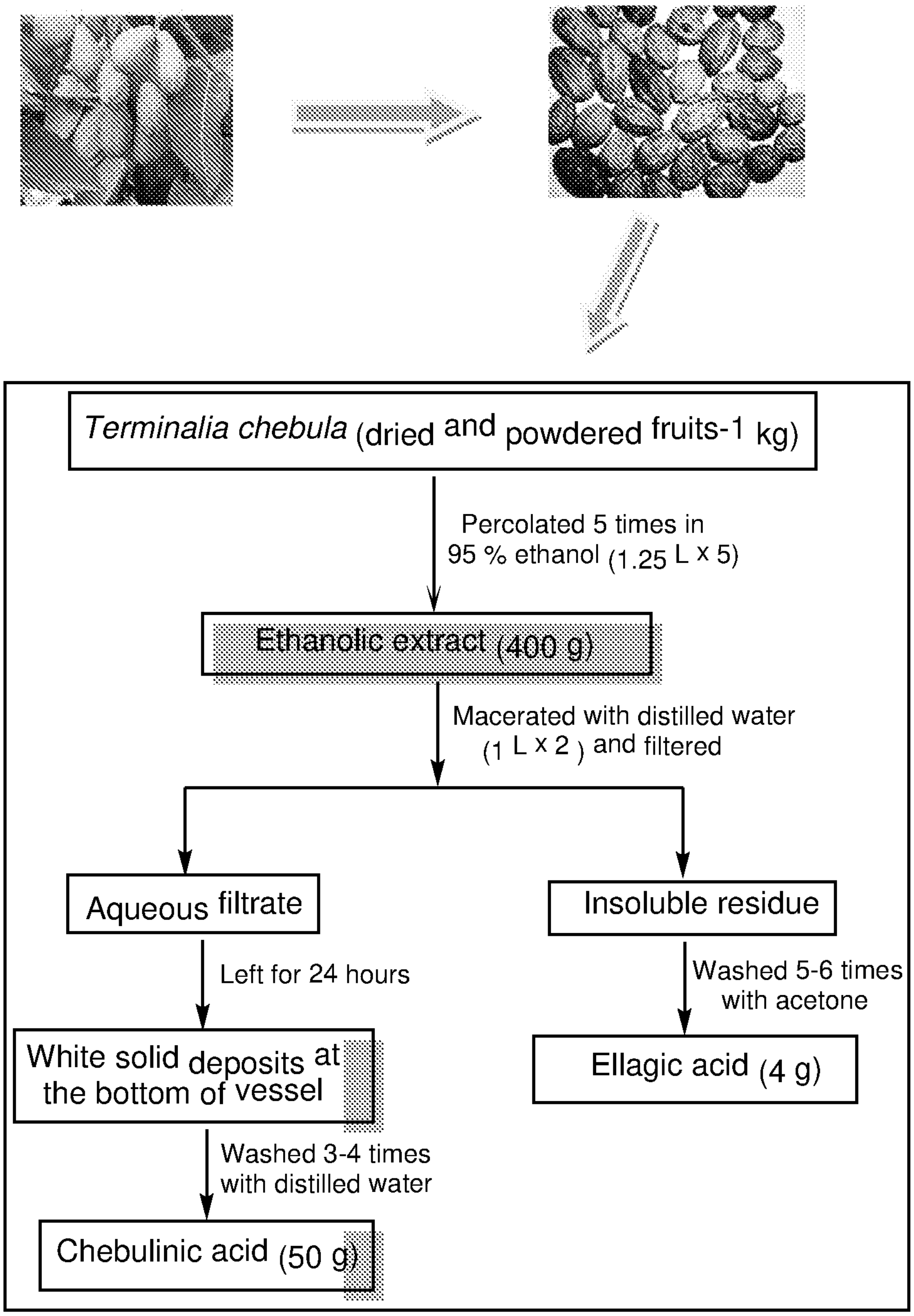
FIG. 1 describes the isolation process for obtaining pure chebulinic acid and ellagic acid from the dried and grinded fruits of *T. chebula*.
Figure 2:
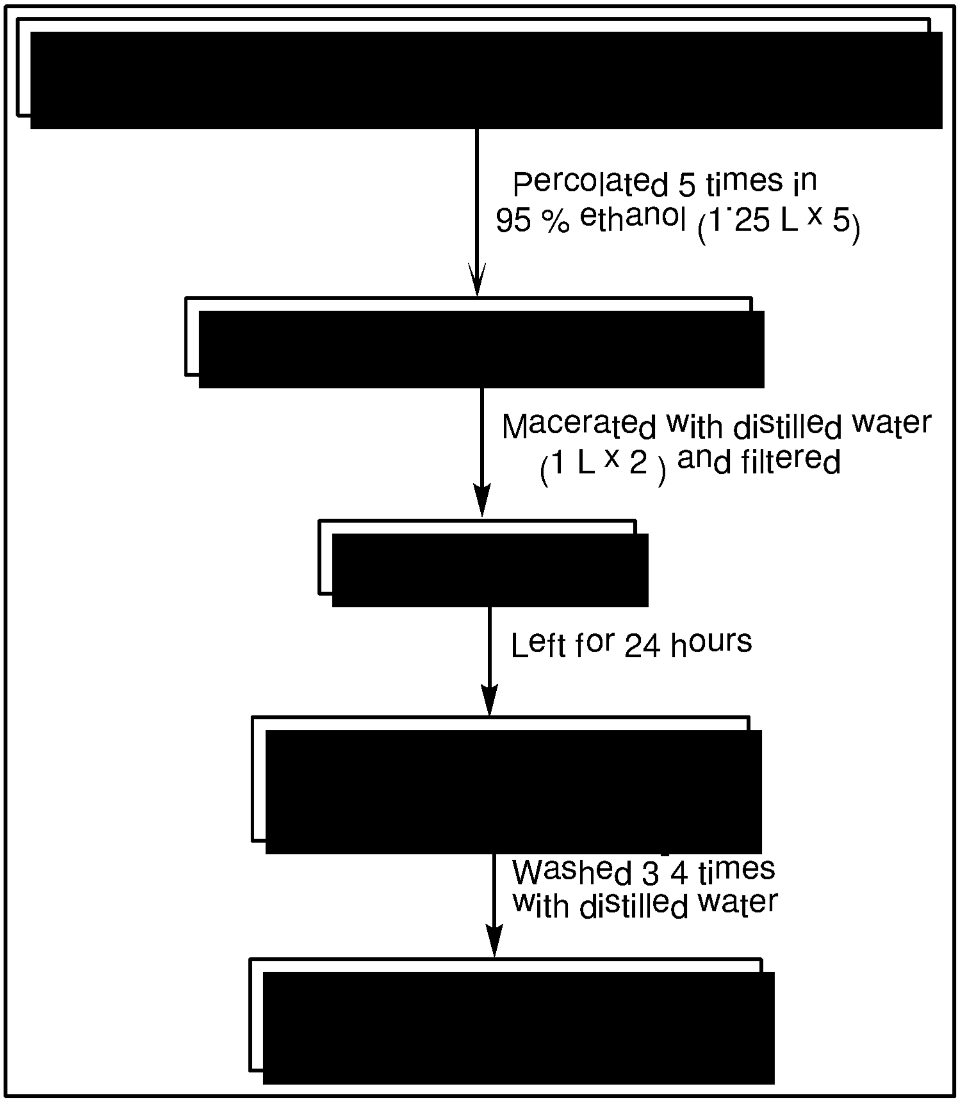
FIG. 2 describes the process of preparation of chebulinic acid enriched fraction from the dried and grinded fruits of *T. chebula*.
Figure 3:
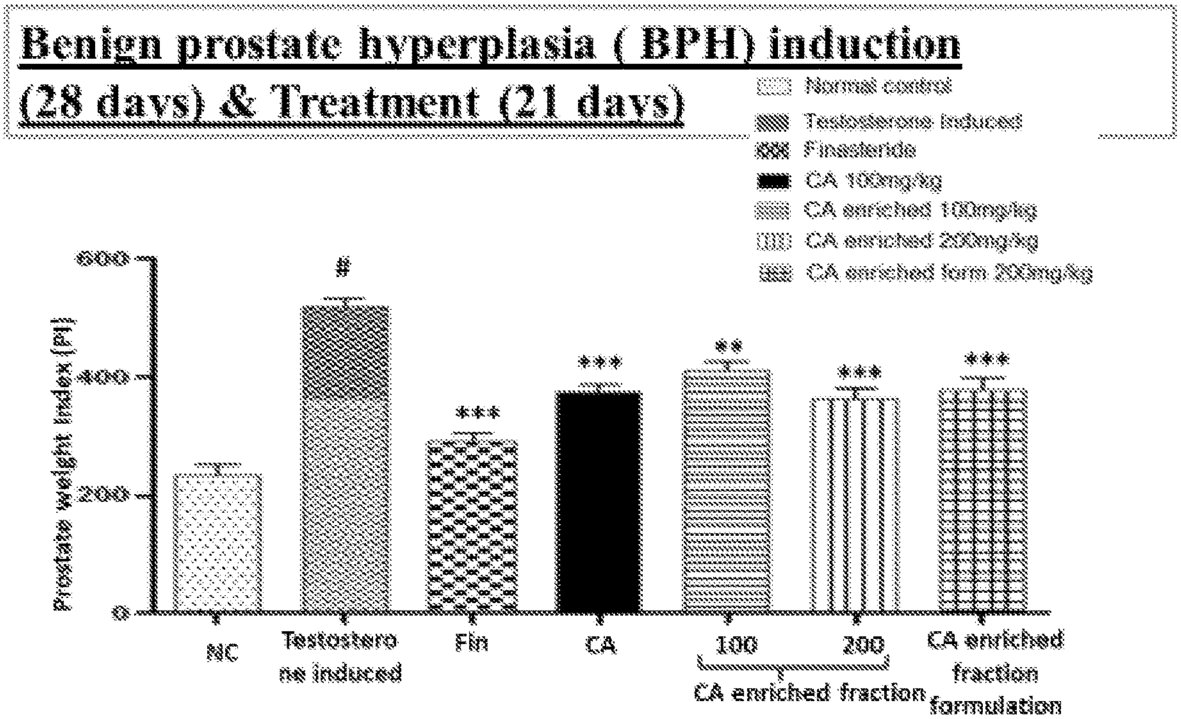
FIG. 3 represents prostate weight index with the treatment of chebulinic acid (CA) and chebulinic acid enriched fraction (CAEF) obtained from *T. chebula* fruits for the management of BPH.

To assess the therapeutic effect of Chebulinic Acid (CA) and Chebulinic acid Enriched fraction (CAEF) on Benign Prostatic Hyperplasia (BPH), rat BPH model has been successfully generated by testosterone induction method. For model induction of BPH, Orchiectomy (Surgical removal of Testis) of rats was performed and then animals were left for ten days to recover. Now BPH was induced through the daily subcutaneous injections of Testosterone (5 mg/kg & 6.25 mg/ml in Corn Oil) at the inguinal region for 28 days continuously. While the treatment group received 7 days continuous administration of Testosterone and then Testosterone+CA (100 mg/kg B.W) or Testosterone+CAEF (100/200 mg/kg B.W.) or Testosterone+Finasteride (3 mg/kg) were administered orally once a day to these animals for next 21 days (FIG. 3). In another experiment the treatment group received 7 days continuous administration of Testosterone and then Testosterone+CAEF (100 mg/kg B.W.) administered orally once a day to these animals for next 4 weeks (group 1) 8 weeks (group 2) and 12 weeks (group 3) (FIG. 6). After that these animals were left for fasting overnight and sacrificed next day; their prostatic as well as other reproductive organs were dissected out. Portions of the prostatic ventral lobes were stored in 4% paraformaldehyde for histological and immuno-histochemical processing. Half of the remaining prostate tissue was stored in RNA later and the other half was stored at −80° C. for subsequent biochemical and molecular experiments. Blood samples were obtained from the caudal vena cava and collected in serum separating tubes.

These blood containing tubes were remained at RT for 2 h and sera were separated by centrifuging at 3000×g for 20 min at 4° C. Collected serum was stored at −80° C. for further assays.

Calculation of Prostate Weight and Prostatic Weight Index (PI)

Testosterone induced BPH animal models were sacrificed after the simultaneous treatment of 21 days. The intact prostate tissue was dissected and removed carefully from these sacrificed animals. Now the prostate weight (PW) was measured and the prostate index (PI) was calculated as PW (mg)/Body Weight (gm)×100.

Histopathological Examination

The prostate tissues were immediately fixed with 4% para-formaldehyde, dehydrated in ascending grades of alcohol, cleared in xylene and embedded in paraffin wax. Paraffin blocks were sectioned at 5 μm thickness. Sectioned tissues were mounted on slides and stained with hematoxylin and Eosin (H & E staining). These sections were evaluated microscopically for histological changes under Primovert microscope (Carl Zeiss, Germany).

Statistical Analysis

Data were expressed as the mean±SEM of four animals per group (n=4 per group). The values were analysed using one-way analysis of variance. Values were considered statistically significant at $p<0.05$.

Results

The Prostate Weight Index Analysis of Prostate Tissue

To observe the induction of BPH in rat model, changes in prostate weight caused by Testosterone were measured after 7 days. The prostate weight index was higher in the Testosterone-induced BPH group within 7 days itself as compared to the control group (FIGS. 3 and 6) which confirmed the authenticity of the BPH rat model.

Administration of Testosterone significantly elevated the total prostate weight index as compared to the normal prostate (FIGS. 3 and 6). Treatment with CA/CAEF significantly decreased the total prostate weight index when compared to the Testosterone induced group.

Prostate weight index (PI) was observed to be highest in the Testosterone induced group which reduced significantly in Testosterone+CA/CAEF treated groups within 21 days (FIG. 3) and 4, 8 and 12 weeks (FIG. 6) of treatment in the induced animal model of BPH. The PI of Finasteride group was close to the 200 mg/kg CA/CAEF treated group (FIG. 3). Comparison between the testosterone induced model and treatment group showed that there was a significant recovery in prostatic weight index of CA/CAEF treated group in a dose dependent manner and 100/200 mg/kg dose (FIG. 3) and 100 mg/kg of CAEF (FIG. 6) was quite close to the normal control group.

Histopathological Analysis

Evaluation for changes in the histomorphology of the prostate tissues was done by hematoxylin & eosin (H&E) staining. The Testosterone treatment group produced a significant increase in the epithelial thickness of the prostates at week 4 as compared to the normal rat.

However, treatment with CAEF considerably decreased the epithelial thickness as compared to the Testosterone treated group (FIG. 4). Administration of Testosterone reduced the prostatic lumen area of the prostate when compared with the normal group. However, treatment with CA/CAEF (100/200 mg/kg) increased prostatic lumen areas significantly as compared to the Induced BPH group (FIG. 4).

The results of the present study authenticated the induced rat model of BPH. This was evidenced by increase in prostate weight, histological condition of prostate tissues. The integrity of prostate from BPH induced rats was highly compromised based on the findings from histological analyses. Induced rat model of BPH showed a significant increase in the prostate weight as compared to the control rats. This observation was consistent that linked the increase to stromal-epithelial interaction within the tissue. Treatment with Chebulinic acid (CA)/Chebulinic Acid Enriched fraction (CAEF) significantly suppressed the development of prostatic hyperplasia and the prostatic weight reduced significantly, besides histological indices were affected.

Histopathological examination of BPH rats revealed glandular hyperplasia of the prostate accompanied with numeral secretions, whereas the rats treated with CA/CAEF showed mild glandular hyperplasia.

Hence our result suggests that CA/CAEF inhibit the development and progression of BPH induced by Testosterone. Thus, CA/CAEF can have therapeutic applications in elderly subjects of BPH.

CA/CAEF showed its positive effect for benign prostatic hyperplasia (BPH) in the rat model. The present study confirmed that daily administration of low testosterone in castrated rats for 28 days was able to induce similar condition in rat that is closely related to BPH in humans. This was evidenced by increase in prostate weight, increase PSA (FIGS. 5 and 7) & testosterone serum level, various markers' expression and histopathological condition of prostate tissue. The integrity of prostate from BPH induced rats was highly compromised based on the findings from histological analyses. Interestingly, treatment of BPH induced rats with CA/CAEF caused a significant reduction in prostatic weight (FIGS. 3 and 6) and improved histological conditions (FIG. 4). Treatment with CA/CAEF suppressed the development of prostatic hyperplasia considerably and histological indices were affected. This treatment also showed reduced level of PSA and testosterone in their sera (FIGS. 5 and 7). Number of anti-apoptotic markers were found to be down-regulated after the treatment of Chebulinic acid, which reflects the mechanism of treatment through increased apoptosis [FIGS. 8-13].

After the CAEF treatment; systematic observations within four, eight and twelve weeks, increased apoptosis was also predicted through the differentially regulated Enzymatic and Hormonal pathways [FIGS. 14-16].

Overall, these results suggest that administration of Chebulinic acid to BPH induced rats decreased the prostate weight and restored the altered histological architecture of the prostate. Hence, CA/CAEF could have enormous clinical applications in elderly subjects of BPH.

We claim:

1. A pharmaceutical composition comprising:

(a) a chebulinic acid enriched fraction (CAEF) comprising:

i. Chebulinic acid (CA) present in an amount of 50% to 80% w/w, with a purity of 95% to 98%; and ii. Ellagic acid (EA) present in an amount of 5% to 10% w/w;

iii. and (b) one or more pharmaceutically acceptable additives selected from excipients, adjuvants, solvents, carriers, flavouring agents, colouring agents or coatings, present in an amount of 20% to 50% w/w.

2. The composition of claim 1, wherein the composition is for the treatment of prostatic hyperplasia without significantly affecting histological indices, and wherein the composition comprising chebulinic acid enriched fraction comprises chebulinic acid in an amount of 60% to 80% w/w.

3. A process for preparing the comprising Chebulinic acid (CA) and Ellagic acid (EA), the process comprising the steps of:

a) grinding fruit of the *Terminalia chebula* plant to obtain a powder;

b) extracting the powder obtained in step (a) with 6.5 liters of 95% solvent to produce an extract;

c) drying the extract obtained in step (b) to obtain a dried powder;

d) macerating the powder obtained in step (c) with water and allowing the powder to stand for 48 to 50 hours at a temperature in the range of 20° C. to 30° C., followed by filtration to obtain a Chebulinic Acid Enriched Fraction CAEF;

e) washing the CAEF obtained in step (d) with water to isolate CA and a water-insoluble extract;

f) washing the water insoluble extract obtained in step (e) with acetone to isolate EA; and g) combining the isolated CA and EA to form the composition.

4. The process of claim 3, wherein the solvent used is selected from ethanol or methanol.

5. The process of claim 3, wherein the yield of the CA is in the range of 10% to 15% with purity in the range of 95% to 98%.

6. The process of claim 3, wherein the CAEF comprises CA in an amount greater than 50% by weight.

7. The composition of claim 1, wherein the composition is administered orally in capsule, caplet, tablet or syrup dosage forms.

8. A method of treating benign prostatic hyperplasia in a subject in need thereof, the method comprising administering to the subject an effective amount of the composition of claim 1.

9. The composition of claim 1, wherein the CA and EA are both obtained from dried fruits of *Terminalia chebula*.

10. The process of claim 3, further comprising adding one or more pharmaceutically acceptable additives selected from excipients, adjuvants, solvents, carriers, flavouring agents, colouring agents or coatings, wherein the additives are present in an amount ranging from 20% to 50% by weight of the composition.

11. The process of claim 3, wherein the isolated Chebulinic acid (CA) present in the composition is in an amount ranging from 50% to 80% by weight.

12. The process of claim 3, wherein the isolated Ellagic acid (EA) present in the composition is in an amount ranging from 5% to 10% by weight.

* * * * *